United States Patent
Kobayashi (10) Patent No.: US 11,553,890 B2
(45) Date of Patent: Jan. 17, 2023

(54) RADIATION IMAGING APPARATUS, RADIATION IMAGING SYSTEM, CONTROL METHOD FOR RADIATION IMAGING APPARATUS, AND NON-TRANSITORY COMPUTER-READABLE STORAGE MEDIUM

(71) Applicant: CANON KABUSHIKI KAISHA, Tokyo (JP)

(72) Inventor: Shigeo Kobayashi, Kanagawa (JP)

(73) Assignee: CANON KABUSHIKI KAISHA, Tokyo (JP)

(*) Notice: Subject to any disclaimer, the term of this patent is extended or adjusted under 35 U.S.C. 154(b) by 91 days.

(21) Appl. No.: 17/319,372

(22) Filed: May 13, 2021

(65) Prior Publication Data
US 2021/0369227 A1 Dec. 2, 2021

(30) Foreign Application Priority Data
May 26, 2020 (JP) .............................. JP2020-091443

(51) Int. Cl.
*A61B 6/00* (2006.01)
(52) U.S. Cl.
CPC .............. *A61B 6/54* (2013.01); *A61B 6/5205* (2013.01)
(58) Field of Classification Search
CPC ........ H01L 27/14612; H01L 27/14645; H04N 5/378; H04N 5/361; G01T 7/005; A61B 6/54; A61B 6/5205
See application file for complete search history.

(56) References Cited

U.S. PATENT DOCUMENTS

| 10,742,911 B2 | 8/2020 | Kobayashi |
| 2020/0135780 A1* | 4/2020 | Hayashida ............... H04N 5/32 |
| 2020/0166656 A1 | 5/2020 | Kobayashi |

FOREIGN PATENT DOCUMENTS

JP 2016-198209 A 12/2016

* cited by examiner

*Primary Examiner* — Don K Wong
(74) *Attorney, Agent, or Firm* — Venable LLP (57) ABSTRACT

A radiation imaging apparatus comprising a first memory storing first gain correction data corresponding to imaging modes, a second memory having a higher read speed than the first memory, and a controller being able to perform imaging in the imaging modes is provided. The controller stores second gain correction data based on the first gain correction data in the second memory after startup, and when an imaging request is issued from startup to storage of all the second gain correction data into the second memory and requested gain correction data which corresponds to a requested imaging mode has been stored in the second memory, performs acquisition of radiation image data and offset correction data in the requested imaging mode and correction for the radiation image data by using the offset correction data and the requested gain correction data stored in the second memory.

15 Claims, 6 Drawing Sheets

| IMAGING MODE NUMBER | FIELD ANGLE [cm] | FRAME RATE [fps] | SENSITIVITY |
|---|---|---|---|
| 1 | 43×43 | 30 | High |
| 2 | 15×15 | 15 | High |
| 3 | 30×30 | 30 | Mid |
| 4 | 30×30 | 15 | Mid |
| 5 | 15×15 | 8 | Low |
| ⋮ | ⋮ | ⋮ | ⋮ |

FIG. 4

| PRIORITY | IMAGING MODE NUMBER |
|---|---|
| PREFERENCE IMAGING MODE | 1 |
| | 5 |
| | 10 |
| | ⋮ |
| ORDINARY IMAGING MODE | 2 |
| | 3 |
| | 4 |
| | ⋮ |

| DEPLOYMENT ORDER | IMAGING MODE NUMBER |
|---|---|
| 1 | 1 |
| 2 | 5 |
| 3 | 10 |
| 4 | 2 |
| 5 | 3 |
| 6 | 4 |
| 7 | 6 |
| : | : |

FIG. 9

RADIATION IMAGING APPARATUS, RADIATION IMAGING SYSTEM, CONTROL METHOD FOR RADIATION IMAGING APPARATUS, AND NON-TRANSITORY COMPUTER-READABLE STORAGE MEDIUM

BACKGROUND OF THE INVENTION

Field of the Invention

The present invention relates to a radiation imaging apparatus, a radiation imaging system, a control method for the radiation imaging apparatus, and a non-transitory computer-readable storage medium.

Description of the Related Art

Radiation imaging apparatuses are widely used in medical image diagnosis and non-destructive inspection. Japanese Patent Laid-Open No. 2016-198209 discloses a radiation imaging apparatus that can perform imaging in a plurality of imaging modes such as moving image capturing or still image capturing. Offset correction and gain correction are performed in imaging in a plurality of imaging modes to obtain radiation images suitable for the respective imaging modes. Data for offset correction is acquired without irradiation with radiation after the power supply of the radiation imaging apparatus is turned on because characteristics such as an offset amount tend to change depending on an environment such as temperature. Since data for gain correction is robust against the influences of temperature and the like, the data can be recorded in a nonvolatile memory or the like in advance and used by being read out into a fast memory for arithmetic processing after the power supply of the radiation imaging apparatus is turned on. As the number of imaging modes increases, it takes more time to acquire data for offset correction and read out data for gain correction, resulting in a longer time to be ready for imaging from when the power supply of the radiation imaging apparatus is turned on. Japanese Patent Laid-Open No. 2016-198209 discloses a technique of making imaging preparations including acquiring data for offset correction and reading out data for gain correction into a fast memory in accordance with imaging modes in descending order of priority. Even while imaging preparations are in progress, imaging is permitted in an imaging mode for which imaging preparations have been completed.

SUMMARY OF THE INVENTION

According to Japanese Patent Laid-Open No. 2016-198209, after the power supply is turned on, data for offset correction in all the imaging modes are acquired, and hence it can take much time until the completion of imaging preparations in all the imaging modes. In addition, the characteristics of offset correction tend to change depending on an environment such as temperature. For this reason, after data for offset correction is acquired, characteristics such as the offset amount may change by the time when actual imaging is performed.

Some embodiments of the present invention provide a technique advantageous in reducing the time until imaging can be performed by a radiation imaging apparatus and improving the quality of an acquired radiation image.

According to some embodiments, a radiation imaging apparatus comprising: a first memory storing in advance a plurality of first gain correction data respectively corresponding to a plurality of imaging modes; a second memory having a higher read speed than the first memory; and a control unit being able to perform imaging in the plurality of imaging modes, wherein the control unit stores, in the second memory, a plurality of second gain correction data respectively corresponding to the plurality of first gain correction data based on the plurality of first gain correction data stored in the first memory after startup of the radiation imaging apparatus, and when an imaging request is issued by a user in a storage period from startup of the radiation imaging apparatus to storage of all the second gain correction data into the second memory and requested gain correction data, of the plurality of second gain correction data, which corresponds to a requested imaging mode associated with the imaging request has been stored in the second memory, performs acquisition of radiation image data and offset correction data in the requested imaging mode and correction processing for the radiation image data by using the offset correction data and the requested gain correction data stored in the second memory, is provided.

According to some other embodiments, a control method for a radiation imaging apparatus including a first memory storing in advance a plurality of first gain correction data respectively corresponding to a plurality of imaging modes and a second memory having a higher read speed than the first memory and able to perform imaging in the plurality of imaging modes, the method comprising: storing, in the second memory, all second gain correction data respectively corresponding to the plurality of first gain correction data based on the plurality of first gain correction data stored in the first memory after startup of the radiation imaging apparatus, and when an imaging request is issued by a user in the storing and requested gain correction data, of the plurality of second gain correction data, which corresponds to a requested imaging mode associated with the imaging request has been stored in the second memory, performing acquisition of radiation image data and offset correction data in the requested imaging mode and correction processing for the radiation image data by using the offset correction data and the requested gain correction data stored in the second memory, is provided.

According to still other embodiments, a non-transitory computer-readable storage medium storing a program for causing a computer to execute a control method of a radiation imaging apparatus including a first memory storing in advance a plurality of first gain correction data respectively corresponding to a plurality of imaging modes and a second memory having a higher read speed than the first memory and able to perform imaging in the plurality of imaging modes, the method comprising: storing, in the second memory, all second gain correction data respectively corresponding to the plurality of first gain correction data based on the plurality of first gain correction data stored in the first memory after startup of the radiation imaging apparatus, and when an imaging request is issued by a user in the storing and requested gain correction data, of the plurality of second gain correction data, which corresponds to a requested imaging mode associated with the imaging request has been stored in the second memory, performing acquisition of radiation image data and offset correction data in the requested imaging mode and correction processing for the radiation image data by using the offset correction data and the requested gain correction data stored in the second memory, is provided.

Further features of the present invention will become apparent from the following description of exemplary embodiments (with reference to the attached drawings).

DESCRIPTION OF THE EMBODIMENTS

Hereinafter, embodiments will be described in detail with reference to the attached drawings. Note, the following embodiments are not intended to limit the scope of the claimed invention. Multiple features are described in the embodiments, but limitation is not made to an invention that requires all such features, and multiple such features may be combined as appropriate. Furthermore, in the attached drawings, the same reference numerals are given to the same or similar configurations, and redundant description thereof is omitted.

Radiation according to the present invention can include not only α-rays, β-rays, and γ-rays that are beams generated by particles (including photons) emitted by radioactive decay but also beams having equal or more energy, for example, X-rays, particle rays, and cosmic rays.

Figure 1:
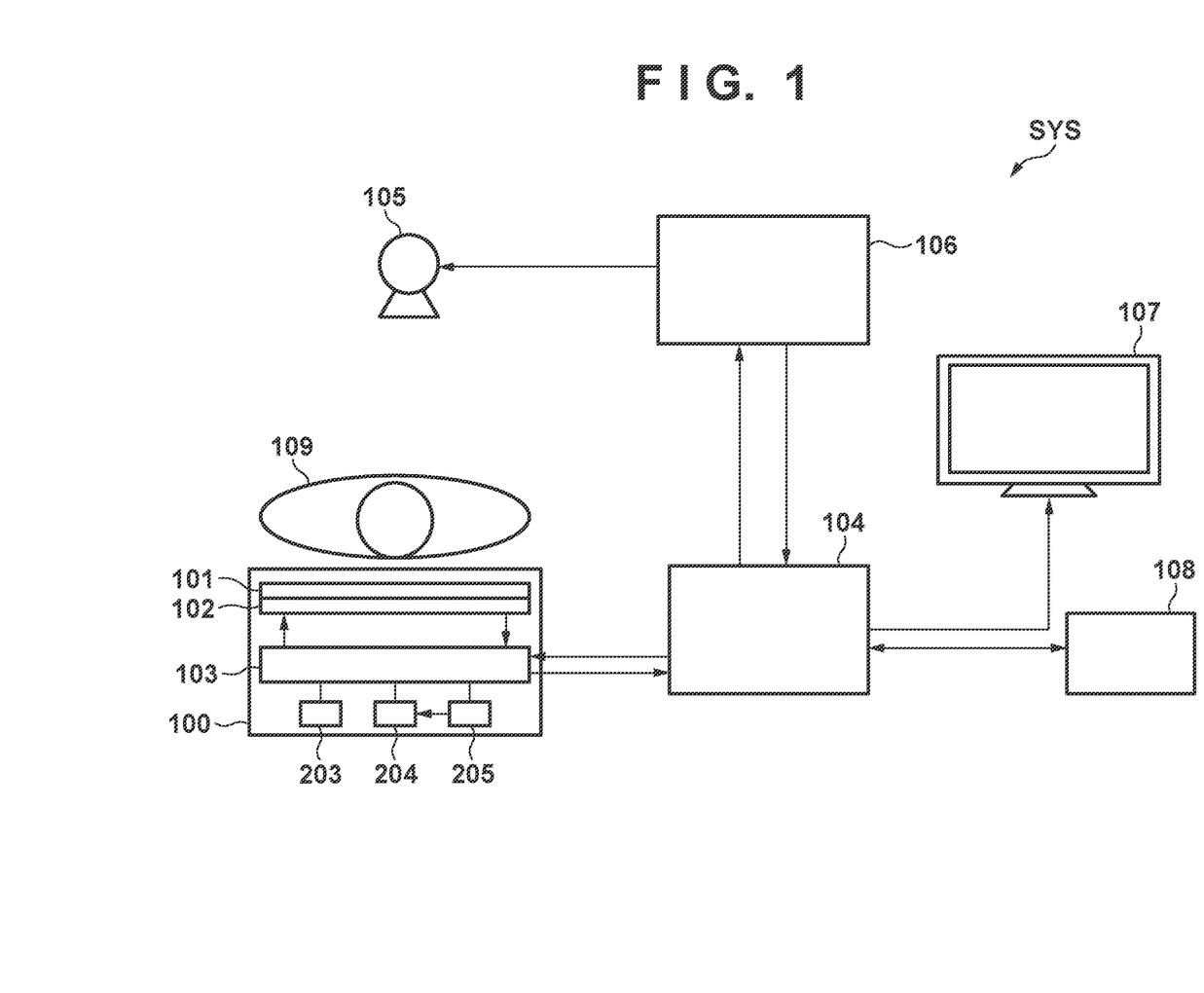
FIG. 1 is a view showing an example of the arrangement of a radiation imaging system including a radiation imaging apparatus according to an embodiment.

The arrangement and operation of a radiation imaging apparatus according to this embodiment will be described with reference to FIGS. 1 to 7. FIG. 1 is a system block diagram showing an example of the overall arrangement of a radiation imaging system SYS including a radiation imaging apparatus 100 according to the first embodiment. The radiation imaging system SYS includes the radiation imaging apparatus 100, a computer 104, a radiation generator 105, a radiation controller 106, a display device 107, and a control console 108 and is configured to image an object 109.

The radiation imaging apparatus 100 includes a scintillator 101, an imaging panel 102, a control unit 103, and memories 203, 204, and 205. The scintillator 101 is a conversion unit that converts radiation into light in a wavelength band which can be detected by the detection elements arranged on the imaging panel 102. The control unit 103 has a function of controlling the overall radiation imaging apparatus 100. More specifically, the control unit 103 has a regulator function of receiving the supply of power from an external power supply or built-in battery (not shown) and supplying power to the overall radiation imaging apparatus 100. The control unit 103 also has a function of driving the imaging panel 102, a function of reading out the radiation image data acquired by the imaging panel 102, and a function of performing correction processing for the radiation image data read out from the imaging panel 102. The correction processing performed by the control unit 103 includes offset correction and gain correction. As offset correction, there is known a method of correcting radiation image data by using image data acquired without irradiation with radiation as offset correction data. As gain correction, there is known a method of correcting radiation image data by using, as gain correction data, image data acquired by irradiation with radiation without through the object 109.

The computer 104 has a function of controlling the overall radiation imaging system SYS in accordance with, for example, the settings made by the user. The user inputs settings such as an imaging mode at the time of capturing a radiation image to the computer 104 via the control console 108. The computer 104 controls the radiation imaging apparatus 100 and the radiation controller 106 in accordance with the set imaging mode. The radiation controller 106 makes the radiation generator 105 operate under the control of the computer 104. The radiation generator 105 irradiates the radiation imaging apparatus 100 with radiation under the control of the radiation controller 106.

Figure 2:
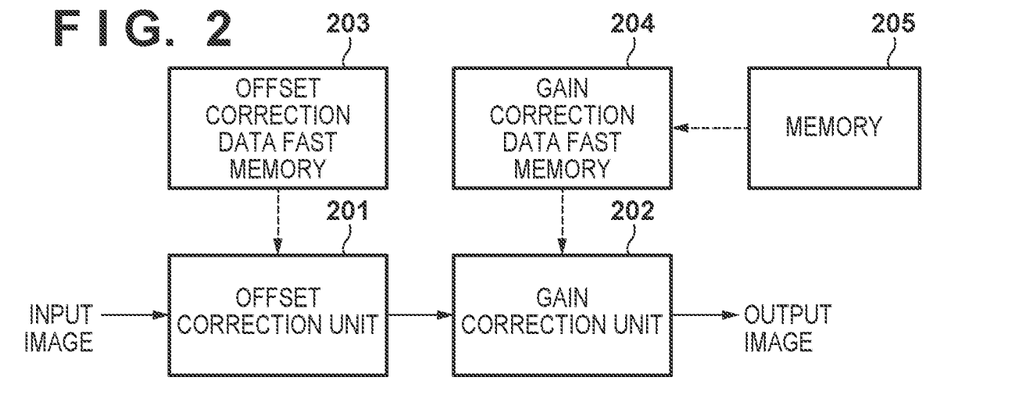
FIG. 2 is a block diagram for explaining the image data correcting operation of the radiation imaging apparatus in FIG. 1.

FIG. 2 is a block diagram showing the arrangement of the memories 203, 204, and 205 of the radiation imaging apparatus 100 and a procedure for correction processing by the control unit 103. A plurality of first gain correction data respectively corresponding to a plurality of imaging modes are stored in advance in the memory 205 to allow the radiation imaging apparatus 100 to perform imaging in the plurality of imaging modes. The control unit 103 stores a plurality of second gain correction data respectively corresponding to the plurality of first gain correction data in the memory 204 based on the plurality of first gain correction data stored in the memory 205 after the startup of the radiation imaging apparatus 100. In this case, second gain correction data corresponding to data of interest of the first gain correction data will be referred to as corresponding data. At this time, data of interest may be identical to corresponding data. That is, corresponding data stored in the memory 204 may be data obtained by transferring data of interest stored in the memory 205. In addition, for example, data of interest may be data obtained by compressing corresponding data, and the control unit 103 may store the corresponding data obtained by decompressing and deploying the data of interest in the memory 204. The memory 204 is a fast memory having a higher read speed than the nonvolatile memory 205, and can be, for example, a volatile memory. When data stored in the memory 205 is discriminated from data stored in the memory 204, the respective data will be referred to as "first gain correction data" and "second gain correction data" as described above. In addition, when the respective data are simply referred to as "gain correction data", the data means data stored in the memory 204 and used for gain correction.

Offset correction data for offset correction is acquired when radiation image data is acquired upon issuing of an imaging request by the user and stored in the memory 203. The memory 203 is a fast memory having a higher read speed than the nonvolatile memory 205, and can be, for example, a volatile memory. According to the arrangements shown in FIGS. 1 and 2, the memory 203 and the memory 204 are shown as separate components. However, this is not exhaustive, and one memory may function as the memory 203 and the memory 204.

When the user issues an imaging request, the control unit 103 acquires radiation image data and offset correction data. The offset correction data is stored in the memory 203. The control unit 103 then performs correction processing for the radiation image data by using the offset correction data stored in the memory 203 and the second gain correction data stored in the memory 204. For example, as shown in FIG. 2, an offset correction unit 201 of the control unit 103 performs offset correction processing by using the offset correction data stored in the memory 203 for radiation image data read out from the imaging panel 102 as an input image. Subsequently, a gain correction unit 202 of the control unit 103 performs gain correction processing using the gain correction data stored in the memory 204, and transfers the resultant data as an output image to the computer 104.

Figure 3:
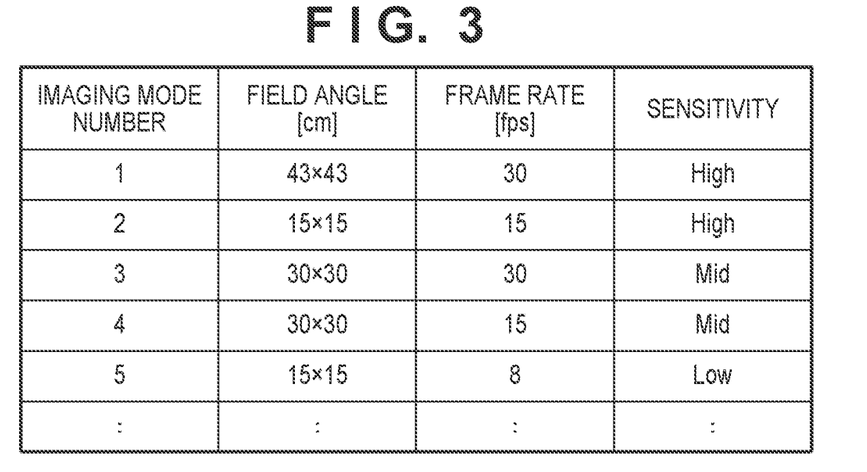
FIG. 3 is a view showing the imaging modes of the radiation imaging apparatus in FIG. 1.
Figure 4:
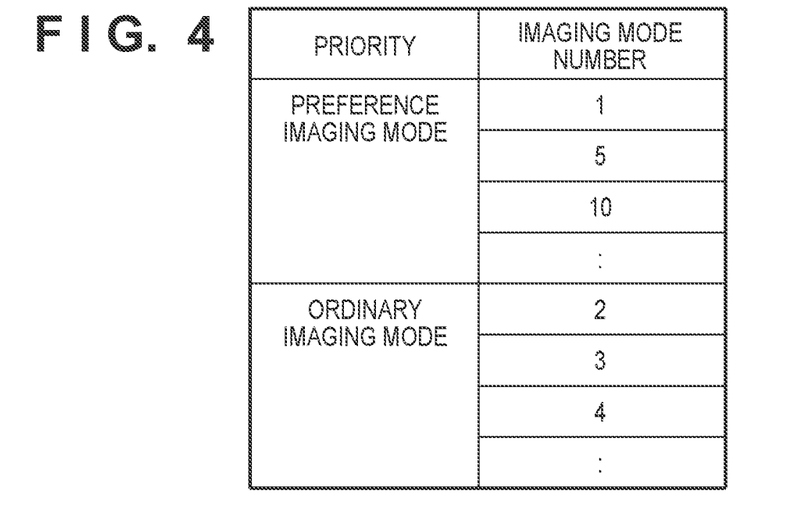
FIG. 4 is a view showing the degrees of priority of the imaging modes of the radiation imaging apparatus in FIG. 1.

The imaging modes of the radiation imaging apparatus 100 will be described next with reference to FIGS. 3 and 4. FIGS. 3 and 4 show an example of imaging modes that can be edited and used by the user in accordance with usage conditions and the like. FIG. 3 is a table showing a list of imaging modes in which the radiation imaging apparatus 100 can perform imaging. The radiation imaging apparatus 100 has a plurality of imaging modes each of which has a combination of a field angle, a frame rate, a sensitivity, and the like corresponding to an imaging technique. Each imaging mode is assigned with an imaging mode number to be managed. First gain correction data is linked to this imaging mode number and stored in the nonvolatile memory 205. FIG. 4 shows an example of grouping the imaging modes shown in FIG. 3 according to priority. Referring to FIG. 3, imaging modes that need to be used immediately after the startup of the radiation imaging apparatus 100 are classified as a preference imaging mode group, and the remaining imaging modes are classified as an ordinary imaging mode group. Grouping between the preference imaging mode group and the ordinary imaging mode group may be performed at the time of shipment or can be performed by the user in accordance with the usage condition of the radiation imaging apparatus 100.

Figure 5:
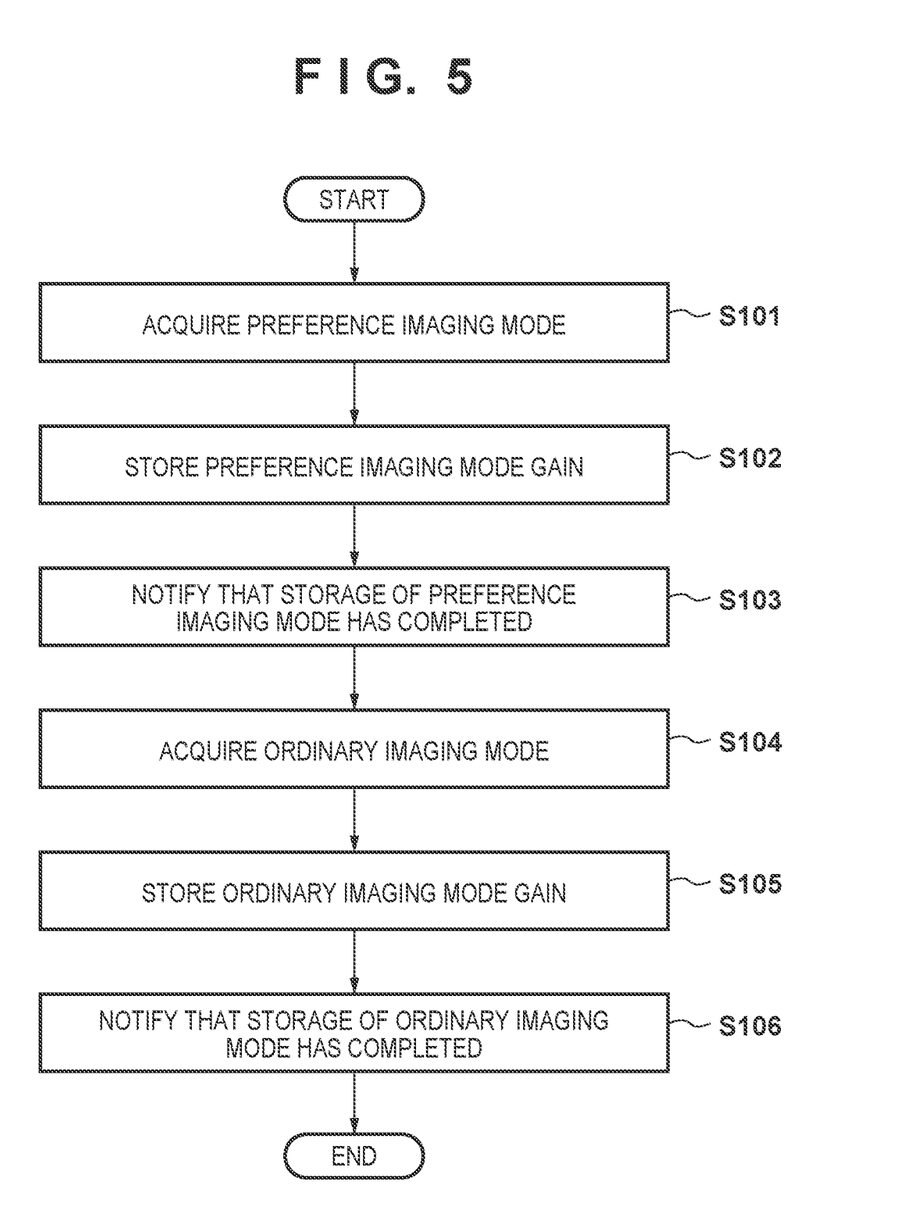
FIG. 5 is a flowchart showing an outline of gain correction data deployment processing by the radiation imaging apparatus in FIG. 1.

The next will describe, with reference to the flowchart of FIG. 5, operation of the radiation imaging apparatus 100 in a storage period from the startup of the radiation imaging apparatus 100 to the storage of all gain correction data in the memory 204.

First of all, in step S101, the control unit 103 acquires an imaging mode number belonging to the preference imaging mode group shown in FIG. 4. In step S102, the control unit 103 then reads out data, of the plurality of first gain correction data stored in the memory 205, which corresponds to the imaging mode in the preference imaging mode group in a predetermined order, and stores the second gain correction data corresponding to the first gain correction data in the memory 204 in a predetermined order. When all the gain correction data corresponding to the preference imaging mode group are completely stored in the memory 204, the control unit 103 notifies the computer 104 of the completion of storage of the gain correction data of the preference imaging mode group into the memory 204 (step S103). In accordance with this operation, the computer 104 may notify the completion of storage of all the gain correction data corresponding to the preference imaging mode group into the memory 204 by using the display device 107. In other words, the display device 107 may function as a notification unit of the radiation imaging apparatus 100. Alternatively, for example, the radiation imaging apparatus 100 may include a display and a lamp and make the display and the lamp function as notification units to notify the completion of storage of all the gain correction data corresponding to the preference imaging mode group into the memory 204.

Upon completion of storage of gain correction data corresponding to the preference imaging mode group, the flow shifts to step S104. The control unit 103 then acquires an imaging mode number belonging to the ordinary imaging mode group shown in FIG. 3. In step S105, the control unit 103 reads out data, of the plurality of first gain correction data stored in the memory 205, which corresponds to the ordinary imaging mode group in a predetermined order, and stores the second gain correction data corresponding to the first gain correction data in the memory 204 in a predetermined order. Upon completion of storage of all the gain correction data corresponding to the ordinary imaging mode group into the memory 204, the control unit 103 notifies the computer 104 of the completion of storage of all the gain correction data into the memory 204 (step S106). In accordance with this operation, the computer 104 may notify the completion of storage of all the gain correction data into the memory 204 by using the display device 107. In addition, as described above, the radiation imaging apparatus 100 may include a display and a lamp and notify the completion of storage of all the gain correction data into the memory 204 by making the display or lamp function as a notification unit. With the above operation, the control unit 103 terminates the step of storing all the second gain correction data corresponding to the plurality of first gain correction data into the memory 204 based on the plurality of first gain correction data stored in the memory 205 upon startup of the radiation imaging apparatus 100.

Figure 6:
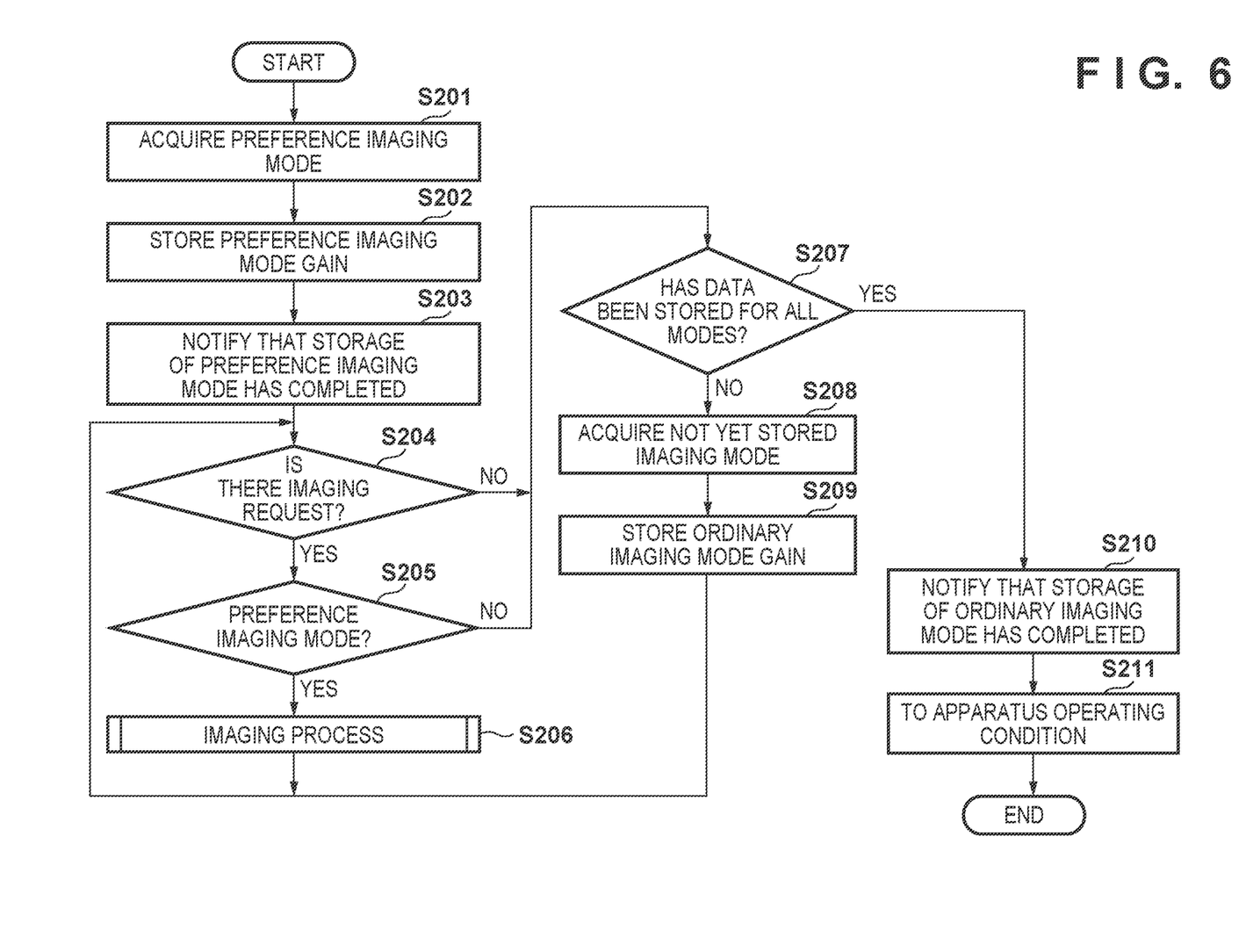
FIG. 6 is a flowchart showing an outline of gain correction data deployment processing by the radiation imaging apparatus in FIG. 1.
Figure 7:
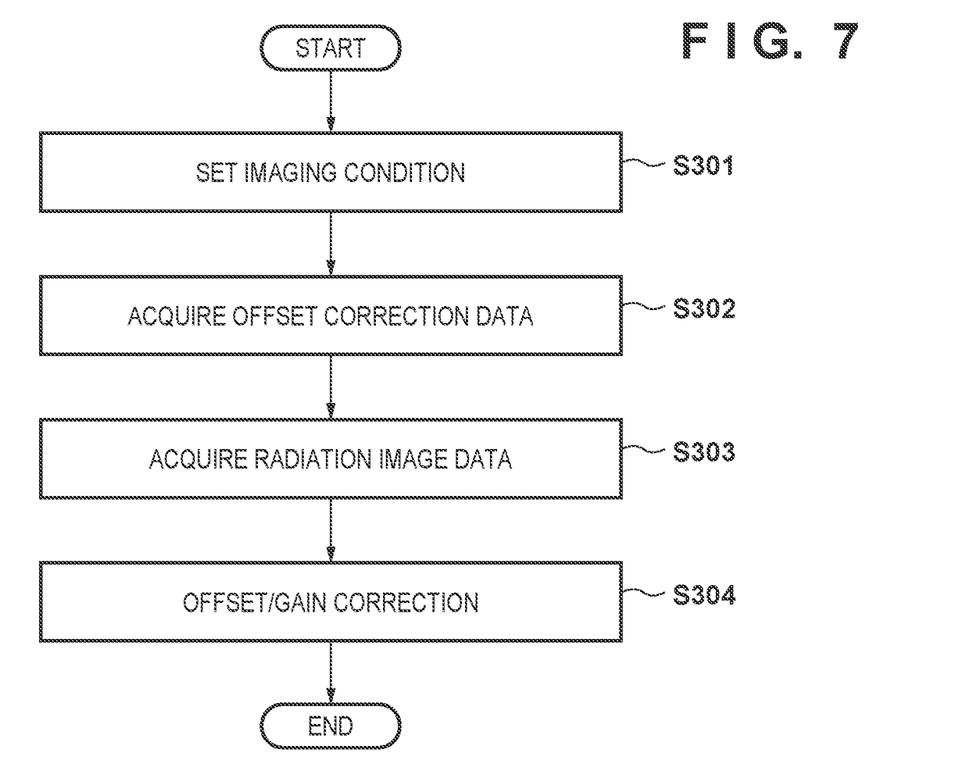
FIG. 7 is a flowchart showing imaging processing by the radiation imaging apparatus in FIG. 1.

The next will describe, with reference to the flowcharts shown in FIGS. 6 and 7, the operation of the radiation imaging apparatus 100 upon receiving an imaging request from the user in a storage period from the startup of the radiation imaging apparatus 100 to the storage of all the gain correction data into the memory 204. Steps S201 to S203 may be performed in a similar manner to steps S101 to S103, and hence a description of them will be omitted.

The control unit 103 notifies the computer 104 of the completion of storage of gain correction data corresponding to the preference imaging mode group into the memory 204, and then determines in step S204 whether an imaging request from the user is received. Upon determining in step S204 that an imaging request from the user is received, the control unit 103 shifts the process to step S205 to determine whether the requested imaging mode associated with the imaging request is included in the preference imaging mode group. Upon determining in step S204 that no imaging request is received from the user, the control unit 103 shifts the process to step S207.

Upon determining in step S205 that the requested imaging mode is included in the preference imaging mode group, the control unit 103 shifts the process to step S206 to execute an imaging process. The imaging process will be described later with reference to FIG. 7. Upon determining in step S205 that the requested imaging mode is not included in the preference imaging mode group, the control unit 103 shifts the process to step S207.

Step S207 and the subsequent steps will be described next. In step S207, the control unit 103 determines whether the gain correction data in all the imaging modes are stored in the memory 204. Upon determining in step S207 that the storage of the gain correction data in all the imaging modes into the memory 204 has not been completed, the control unit 103 shifts the process to step S208. In step S208, the control unit 103 acquires information of an imaging mode, of the ordinary imaging mode group, in which the storage of gain correction data has not been completed. In step S209, the control unit 103 reads out the first gain correction data in the imaging mode obtained in step S208 from the memory 205, and stores the corresponding second gain correction data in the memory 204. After the completion of step S209, the control unit 103 returns the process to step S204 of determining an imaging request from the user, and repeats the steps from step S204.

Upon determining in step S207 that the storage of the gain correction data in all the imaging modes into the memory 204 has been completed, the control unit 103 shifts the process to step S210. As in step S106 described above, in step S210, the control unit 103 notifies the computer 104 of the completion of storage of all the gain correction data into the memory 204. In step S211, the control unit is set in an apparatus operating condition in which the storage period has come to an end and all the imaging modes can be used.

An imaging process in step S206 in FIG. 6 will be described next with reference to FIG. 7. First of all, in step S301, the control unit 103 sets imaging conditions such as a field angle, a frame rate, and a sensitivity corresponding to the requested imaging mode corresponding to an imaging request. In step S302, the control unit 103 then acquires offset correction data by executing imaging without irradiation with radiation and stores the data in the memory 203. In step S303, the control unit 103 acquires radiation image data by imaging the object 109 by irradiating it with radiation. In step S304, the control unit 103 executes the offset correction and the gain correction processing shown in FIG. 2 described above by using the radiation image data obtained in step S303 as an input image, and transfers the objected output image to the computer 104, thus terminating the imaging process. In the flowchart shown in FIG. 7, the radiation imaging apparatus 100 acquires offset correction data in the requested imaging mode before acquiring radiation image data in the requested imaging mode corresponding to the imaging request. However, this is not exhaustive. The radiation imaging apparatus 100 may acquire offset correction data after acquiring radiation image data.

In this embodiment, a plurality of first gain correction data respectively corresponding to a plurality of imaging modes constitute a preference group corresponding to the preference imaging mode group and an ordinary group corresponding to the ordinary imaging mode group, each including one or more gain correction data. After activating the radiation imaging apparatus 100, the control unit 103 stores, in the memory 204, preference group corresponding data of the second gain correction data corresponding to the preference group data based on the preference group data, of the first gain correction data, which is included in the preference group (steps S201 to S203). The control unit 103 then stores, in the memory 204, ordinary group corresponding data of the second gain correction data corresponding to the ordinary group data based on ordinary group data, of the first gain correction data, which is included in the ordinary group (steps S207 to S209). At this time, when an imaging request is issued by the user and requested gain correction data corresponding to a requested imaging mode, of the second gain correction data, which is associated with the imaging request is included in the preference group corresponding data in the period after the preference group data is stored in the memory 204, the control unit 103 starts to acquire radiation image data and offset correction data in the requested imaging mode corresponding to the imaging request (step S206).

As described above, in the radiation imaging apparatus 100, the second gain correction data corresponding to the first gain correction data corresponding to a preference imaging mode, of the imaging modes allowing imaging, which exhibits high priority is stored in the memory 204 in advance. The second gain correction data corresponding to the first gain correction data corresponding to the ordinary imaging mode is then stored in the memory 204. When an imaging request is issued by the user in the preference imaging mode in a period after the second gain correction data corresponding to the first gain correction data corresponding to the preference imaging mode is stored in the memory, radiation image data can be acquired. For this reason, when an imaging request is issued by the user in the preference imaging mode in a period in which the second gain correction data corresponding to the ordinary imaging mode is stored in the memory 204, radiation image data can be acquired. This shortens the time until imaging can be performed in the preference imaging mode after the startup of the radiation imaging apparatus 100. In addition, in this embodiment, when acquiring radiation image data, the radiation imaging apparatus acquires offset correction data. Since the offset amount changes in characteristic depending on an environment such as temperature, acquiring offset correction data before or after the acquisition of radiation image data can cope with a change in characteristic. This can improve the quality of a radiation image after the correction. In this embodiment, after the startup of the radiation imaging apparatus 100, the apparatus does not acquire offset correction data corresponding to all the imaging modes. This can also shorten the time until imaging can be performed in all the imaging modes.

In this embodiment, the control unit 103 may not accept an imaging request from the user until all the preference group corresponding data corresponding to the preference imaging mode group are stored in the memory 204. That is, as shown in FIG. 6, the control unit 103 may not determine whether an imaging request is issued by the user, until the storage of gain correction data in the preference imaging mode group into the memory 204 is completed in step S203 and the process shifts to step S204.

Figure 8:
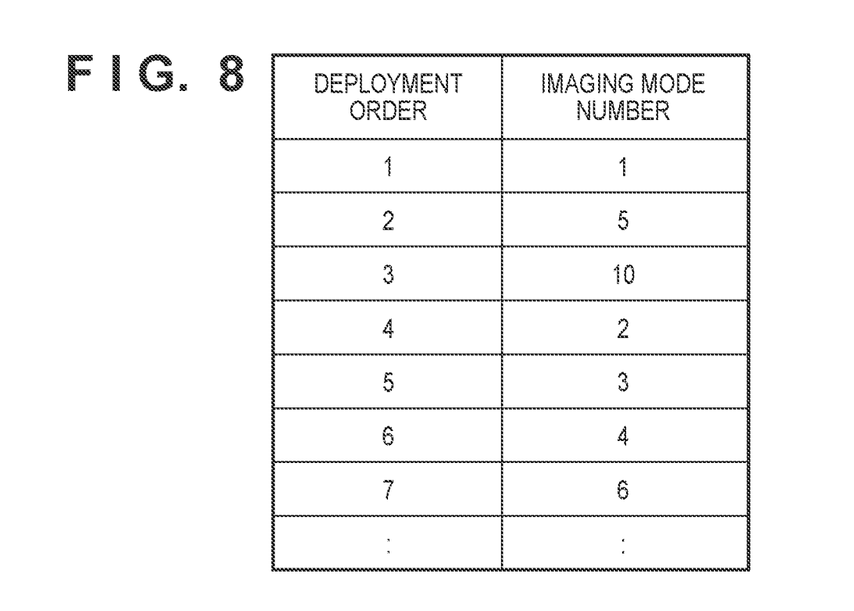
FIG. 8 is a view showing the deployment order of the imaging modes of the radiation imaging apparatus in FIG. 1.
Figure 9:
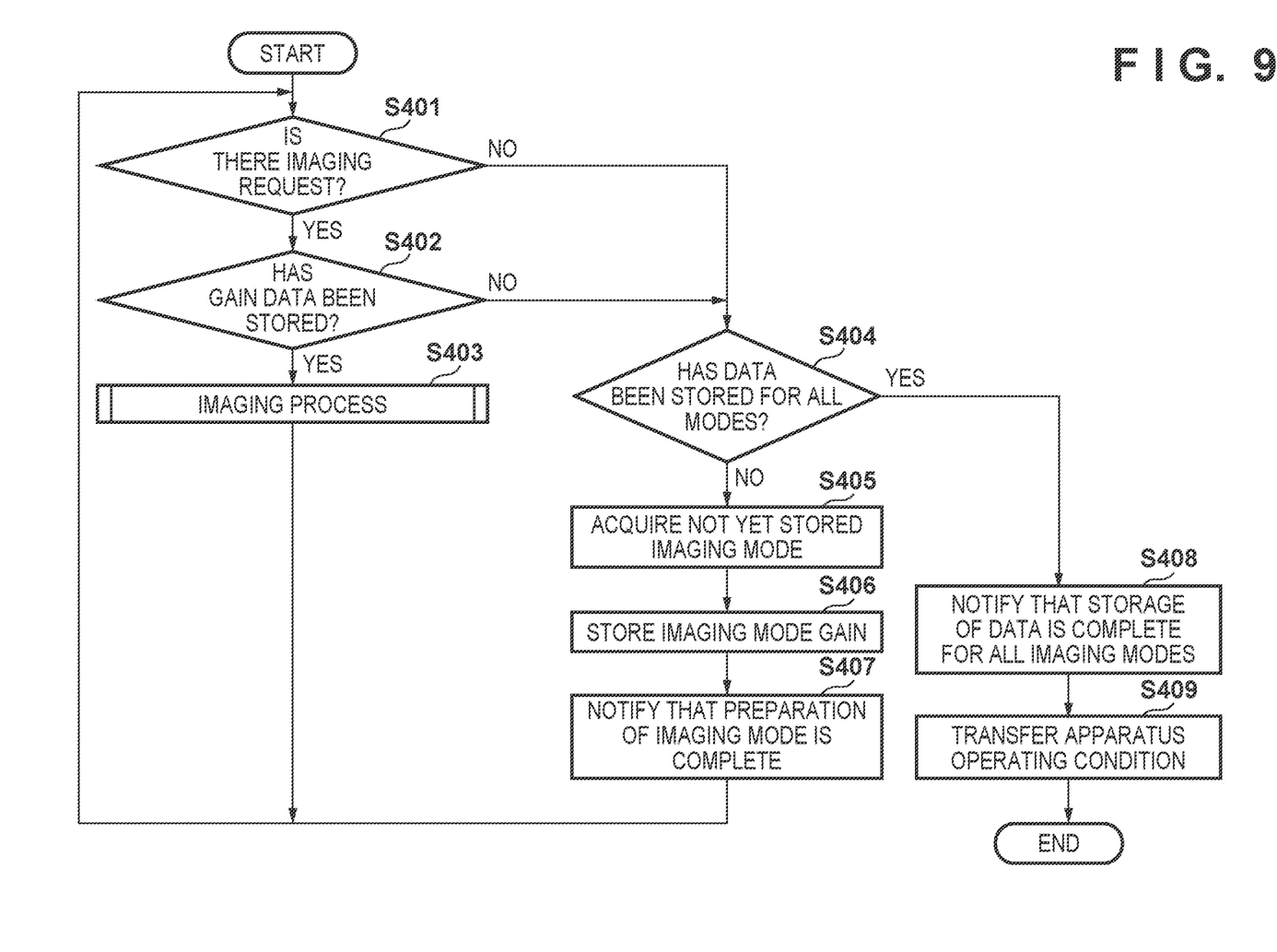
FIG. 9 is a flowchart showing gain correction data deployment processing by the radiation imaging apparatus in FIG. 1.

The following will describe, with reference to FIGS. 8 and 9, a modification of the first embodiment described above of the operation of the radiation imaging apparatus 100 when an imaging request is issued by the user in a storage period from the startup of the radiation imaging apparatus 100 to the storage of all the gain correction data into the memory 204. FIG. 8 is a view showing the order of storage of gain correction data into a memory 204 according to the second embodiment. FIG. 9 is a flowchart for explaining the operation of a radiation imaging apparatus 100 when an imaging request is issued by the user in the storage period from the startup of the radiation imaging apparatus 100 to the storage of all the gain correction data into the memory 204 according to the second embodiment. The arrangement of the radiation imaging apparatus 100 and the types of imaging modes are similar to those in the first embodiment, and hence a description of them will be omitted.

FIG. 8 shows a list of the imaging modes shown in FIG. 3, which are rearranged in the order in which the corresponding information is stored in the memory 204 after the power supply of the radiation imaging apparatus 100 is turned on. A control unit 103 reads out a plurality of first gain correction data stored in a memory 205 in a predetermined order, and stores a plurality of second gain correction data corresponding to the plurality of first gain correction data into the memory 204 in a predetermined order. The user may set the order in which the second gain correction data are stored in the memory 204. The second gain correction data corresponding to an imaging mode with a high use frequency or a high possibility of being used in emergency is stored in the memory 204 first. This can shorten the time until imaging can be performed in an imaging mode with a high use frequency or a high possibility of being used in emergency since the startup of the radiation imaging apparatus 100.

The next will describe, with reference to the flowchart shown in FIG. 9, an operation to be performed when an imaging request is input from the user in the storage period from the startup of the radiation imaging apparatus 100 to the storage of all the gain correction data into the memory 204. After the startup of the radiation imaging apparatus 100, the control unit 103 starts to store a plurality of gain correction data in the memory 204 and determines in step S401 whether an imaging request is issued by the user. Upon determining in step S401 that an imaging request is issued by the user, the control unit 103 shifts the process to step S402. In step S402, the control unit 103 determines whether requested gain correction data, of a plurality of gain correction data, which corresponds to the requested imaging mode associated with the imaging request has been stored in the memory 204. Upon determining in step S401 that no imaging request is issued, the control unit 103 shifts the process to step S404.

Upon determining in step S402 that requested gain correction data corresponding to the imaging mode corresponding to the imaging request has been stored in the memory 204, the control unit 103 shifts the process to step S403 to execute an imaging process. The imaging process in step S403 may be similar to that in step S206 shown in FIG. 6, and each of steps S301 to S304 in FIG. 7 may be performed. Upon determining in step S402 that no requested gain correction data is stored in the memory 204, the control unit 103 shifts the process to step S404.

Step S404 and the subsequent steps will be described next. In step S404, the control unit 103 determines whether gain correction data corresponding to all the imaging modes have been stored in the memory 204.

Upon determining in step S404 that the storage of all the gain correction data into the memory 204 has not been completed, the control unit 103 shifts the process to step S405. In step S405, the control unit 103 acquires information of an imaging mode whose gain correction data has not been completely stored. In step S406, the control unit 103 reads out the first gain correction data in the imaging mode obtained in step S405 from the memory 205, and stores the corresponding second gain correction data in the memory 204. In step S407, the control unit 103 notifies the computer 104 that the imaging mode corresponding to the gain correction data stored in step S406 can be used. In accordance with this operation, the computer 104 may notify the gain correction data, of the plurality of gain correction data, which is stored in the memory 204 by using a display device 107. In other words, the display device 107 may function as a notification unit of the radiation imaging apparatus 100. Alternatively, the radiation imaging apparatus 100 may include a display and a lamp and make the display and the lamp function as notification units to notify the gain correction data, of the plurality of gain correction data, which is stored in the memory 204.

Upon determining in step S402 that no requested gain correction data is stored in the memory 204, the control unit 103 may preferentially read out data corresponding to the requested gain correction data from the memory 205 in the order shown in FIG. 8 and store the data in the memory 204 in steps S405 and S406. In addition, in step S407, the display device 107 or the radiation imaging apparatus 100 may notify with a display, lamp, or the like that requested gain correction data is stored in the memory 204. This can implement a more user-friendly radiation imaging apparatus.

Upon completion of step S407, the control unit 103 returns to step S401 to determine an imaging request from the user and repeats the steps from step S401. Upon determining in step S404 that gain correction data in all the imaging modes have completely been stored in the memory 204, the control unit 103 shifts the process to step S408. In step S408, the control unit 103 notifies the computer 104 of the completion of gain data deployment in all the imaging modes. In accordance with this notification, the computer 104 may notify with the display device 107 that all the gain correction data have been completely stored in the memory 204. Alternatively, as described above, the radiation imaging apparatus 100 may include a display and a lamp and make the display and the lamp function as notification units to notify the completion of storage of all the gain correction data into the memory 204. In step S409, the control unit is set in the apparatus operating condition in which the storage period has come to an end and all the imaging modes can be used.

After the startup of the radiation imaging apparatus 100, based on a plurality of first gain correction data stored in the memory 205, the control unit 103 stores a plurality of second gain correction data respectively corresponding to the plurality of first gain correction data into the memory 204. In this embodiment, when an imaging request is issued by the user in a storage period from the startup of the radiation imaging apparatus 100 to the storage of all the gain correction data into the memory 204 and requested gain correction data, of the gain correction data, which corresponds to the requested imaging mode associated with the imaging request has been stored in the memory 204, the control unit 103 acquires radiation image data and offset correction data in the requested imaging mode. The control unit 103 then performs correction processing for the radiation image data by using the requested gain correction data and offset correction data stored in the memory 204. This can shorten the time until imaging can be performed in an imaging mode with a high use frequency or a high possibility of being used in emergency since the startup of the radiation imaging apparatus 100. In this embodiment as well, when radiation image data is acquired, offset correction data is acquired. This can cope with a change in characteristic such as an offset amount and improve the quality of a radiation image after correction. In addition, in this embodiment as well, after the startup of the radiation imaging apparatus 100, the apparatus does not acquire offset correction data corresponding to all the imaging modes. This can also shorten the time until imaging can be performed in all the imaging modes.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2020-091443, filed May 26, 2020 which is hereby incorporated by reference herein in its entirety.

What is claimed is:

1. A radiation imaging apparatus comprising:
a first memory storing in advance a plurality of first gain correction data respectively corresponding to a plurality of imaging modes;
a second memory having a higher read speed than the first memory, and
a control unit being able to perform imaging in the plurality of imaging modes,
wherein the control unit stores, in the second memory, a plurality of second gain correction data respectively corresponding to the plurality of first gain correction data based on the plurality of first gain correction data stored in the first memory after startup of the radiation imaging apparatus, and
when an imaging request is issued by a user in a storage period from startup of the radiation imaging apparatus to storage of all the second gain correction data into the second memory and requested gain correction data, of the plurality of second gain correction data, which corresponds to a requested imaging mode associated with the imaging request has been stored in the second memory, performs acquisition of radiation image data and offset correction data in the requested imaging mode and correction processing for the radiation image data by using the offset correction data and the requested gain correction data stored in the second memory.

2. The apparatus according to claim 1, wherein the plurality of first gain correction data constitute a first group and a second group each including not less than one gain correction data, and
the control unit stores, based on first group data, of the plurality of first gain correction data, which is included in the first group, in the second memory, first group corresponding data of the plurality of second gain correction data corresponding to the first group data and then stores, based on second group data, of the plurality of first correction data, which is included in the second group, in the second memory, second group corresponding data of the plurality of second gain correction data corresponding to the second group data, and
when an imaging request is issued by the user in a period of the storage period after storage of the first group data into the second memory and the requested gain correction data is included in the first group corresponding data, starts to acquire radiation image data and offset correction data in the requested imaging mode.

3. The apparatus according to claim 2, wherein the control unit accepts no imaging request from the user until all the first group corresponding data is stored in the second memory.

4. The apparatus according to claim 2, further comprising a notification unit configured to notify storage of all the first group corresponding data into the second memory.

5. The apparatus according to claim 2, further comprising a notification unit configured to notify second gain correction data, of the plurality of second gain correction data, which is stored in the second memory in the storage period.

6. The apparatus according to claim 4, wherein the notification unit notifies storage of all the plurality of second gain correction data into the second memory.

7. The apparatus according to claim 1, wherein the apparatus acquires offset correction data in the requested imaging mode before acquiring radiation image data in the requested imaging mode.

8. The apparatus according to claim 1, wherein the control unit reads out the plurality of first gain correction data stored in the first memory in a predetermined order and stores, in the second memory, the plurality of second gain correction data corresponding to the plurality of first gain correction data in the predetermined order, and
the predetermined order can be set by a user.

9. The apparatus according to claim 1, wherein the second memory includes a volatile memory.

10. The apparatus according to claim 1, further comprising a third memory configured to store offset correction data acquired in the requested imaging mode.

11. The apparatus according to claim 10, wherein the third memory has a higher read speed than the first memory.

12. The apparatus according to claim 10, wherein the third memory includes a volatile memory.

13. A radiation imaging system comprising:
the radiation imaging apparatus according to claim 1; and
a radiation generator configured to irradiate the radiation imaging apparatus with radiation.

14. A control method for a radiation imaging apparatus including a first memory storing in advance a plurality of first gain correction data respectively corresponding to a plurality of imaging modes and a second memory having a higher read speed than the first memory and able to perform imaging in the plurality of imaging modes, the method comprising:
storing, in the second memory, all second gain correction data respectively corresponding to the plurality of first gain correction data based on the plurality of first gain correction data stored in the first memory after startup of the radiation imaging apparatus, and
when an imaging request is issued by a user in the storing and requested gain correction data, of the plurality of second gain correction data, which corresponds to a requested imaging mode associated with the imaging request has been stored in the second memory, performing acquisition of radiation image data and offset correction data in the requested imaging mode and correction processing for the radiation image data by using the offset correction data and the requested gain correction data stored in the second memory.

15. A non-transitory computer-readable storage medium storing a program for causing a computer to execute a control method of a radiation imaging apparatus including a first memory storing in advance a plurality of first gain correction data respectively corresponding to a plurality of imaging modes and a second memory having a higher read speed than the first memory and able to perform imaging in the plurality of imaging modes, the method comprising:

storing, in the second memory, all second gain correction data respectively corresponding to the plurality of first gain correction data based on the plurality of first gain correction data stored in the first memory after startup of the radiation imaging apparatus, and when an imaging request is issued by a user in the storing and requested gain correction data, of the plurality of second gain correction data, which corresponds to a requested imaging mode associated with the imaging request has been stored in the second memory, performing acquisition of radiation image data and offset correction data in the requested imaging mode and correction processing for the radiation image data by using the offset correction data and the requested gain correction data stored in the second memory.

* * * * *